United States Patent [19]

Bernstein et al.

[11] 4,104,306
[45] Aug. 1, 1978

[54] 12a-DEOXY CHELOCARDIN

[75] Inventors: Edith Bernstein, Montreal; Daniel Tim-Wo Chu, Dollard des Ormeaux; Stuart Nicholas Huckin, Dorion, all of Canada

[73] Assignee: Abbott Laboratories, North Chicago, Ill.

[21] Appl. No.: 683,570

[22] Filed: May 5, 1976

[51] Int. Cl.² ............................................. C07C 91/16
[52] U.S. Cl. .................................. 260/571; 424/325; 424/330
[58] Field of Search ........................................ 260/571

[56] References Cited

U.S. PATENT DOCUMENTS 4,056,633  11/1977  Kerb et al. ...................... 260/571 X Primary Examiner—Paul F. Shaver
Attorney, Agent, or Firm—Paul D. Burgauer; Robert L. Niblack

[57] ABSTRACT

A new chemical compound, the 12a-deoxychelocardin has been synthesized and found to be a potent antibacterial. It can also be used as an intermediate for the preparation of a number of modified chelocardin analogs that are similarly active as antibacterials, e.g. the compounds carrying different substituents in the D-ring.

3 Claims, No Drawings

12a-DEOXY CHELOCARDIN

DETAILED DESCRIPTION OF THE INVENTION

Chelocardin, formerly identified as M-319 in U.S. Pat. No. 3,155,582 has since been chemically identified as

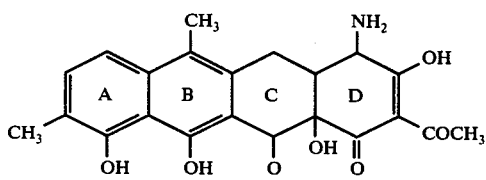

Several modifications in the substituents of the D-ring have produced compounds that have similarly potent antibacterial activities, although the profile of their activity varies somewhat.

It has now been possible to make a new compound, the 12a-deoxychelocardin which differs from the above primarily in the C-ring, which has the following configuration:

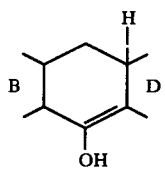

This compound has excellent antibacterial properties, often requiring for inhibiting bacterial growth, a concentration of <10 ppm. In addition, the new compound can be used as intermediate for making the compounds analogous to those that carry different functional groups on the D-ring.

In a general embodiment, the new compound is prepared by protecting the amino group in chelocardin with a suitable, temporary protecting group, i.e. a group that inactivates the hydrogen on the nitrogen and can easily be removed again when desired. The N-protected compound is then reduced and subsequently, the protective group is cleaved in the presence of a strong acid, producing the acid addition salt of the 12a-deoxychelocardin.

In order to show a more specific embodiment, reference is made to the following example which, however, is not to be construed as limiting the invention in any respect. In all instances, the analyses of the intermediate products described below are in excellent agreement with the corresponding calculated values.

EXAMPLE

A solution of 10 g of chelocardin hydrochloride and 20 ml of benzyl chloroformate is made in a mixture of 300 ml of tetrahydrofuran and 60 ml of water. A solution of 15 g of sodium bicarbonate in 250 ml of water is added thereto under vigorous stirring, over a period of approximately 15 minutes. The mixture is acidified with concentrated hydrochloric acid to pH 2.0. The organic layer is separated and concentrated to approximately 50 ml, before being dissolved in 250 ml of chloroform. The chloroform solution is then washed with saturated brine (2 × 30 ml) and dried over anhydrous sodium sulfate. Evaporation under reduced pressure produces 10.7 g (88%) of a yellow, amorphous solid which is essentially pure N-carbobenzoxy chelocardin. Recrystallization from glacial acetic acid (6 ml/g) gives crystalline N-carbobenzoxy chelocardin melting at 206°–211° C.

Zinc dust was activated by vigorous agitation with 1N hydrochloric acid (10 ml/g), rapid filtration, washing with water (3 × 25 ml/g) and acetone (2 × 10 ml/g) and drying under high vacuum.

To a solution of 10 g of carbobenzoxy chelocardin in 500 ml of glacial acetic acid is added 30 g of freshly activated zinc dust. The mixture is stirred at ambient temperature for 18 hours and filtered. The filtrate is diluted with 250 ml of water and the resulting precipitate is collected by filtration. The precipitate is dissolved in 500 ml of chloroform and the solution is washed with saturated brine (3 × 100 ml), dried over anhydrous sodium sulfate and evaporated at reduced pressure to give 7.3 g (74%) of a red solid. Purification of this material is achieved by chromatography on Sephadex LH20 (a partially cross-linked dextran gel which excludes molecular weights of <4000; marketed by Pharmacia of Uppsala, Sweden), using chloroform as eluent to give an amorphous solid having a melting point of 175°–183° C and identified as N-carbobenzoxy-12a-deoxychelocardin.

A solution of 5 g of the unpurified material is dissolved in 30% hydrobromic acid in glacial acetic acid and the solution stirred for 5 minutes. The solution is poured into 500 ml of ether and the resulting precipitate is collected by filtration and dried under high vacuum. The solid is dissolved in 27 ml of methanol and filtered after 30 minutes. The filtrate is diluted to 50 ml with methanol and 2 g of charcoal is added. The resulting suspension is stirred for 1 hour, filtered and concentrated to approximately 20ml. Addition of 30 ml of ethanol and evaporation under reduced pressure gives 2.2 g. of semi-crystalline 12a-deoxychelocardin hydrobromide, melting point 232°–236° C (decomposition).

The antibacterial activity of the above material was tested in the usual fashion, using a two-fold, brain-heart infusion agar (BHI 10 ml/plate) dilution test with 12 different organisms. The following minimum inhibitory concentrations (MIC) were determined:

| Organism | MIC | |
|---|---|---|
| Staph. aureus 45 | 3.1 | p.p.m. |
| Staph. aureus Smith | 3.1 | p.p.m. |
| Enterococcus 89 | 6.2 | p.p.m. |
| Escherichia coli Juhl | 25 | p.p.m. |
| Streptococcus pyrogenes C203 | 6.2 | p.p.m. |
| Klebsiella pneumoniae 8045 | 6.2 | p.p.m. |
| Pasteurella multocida 10544 | 0.39 | p.p.m. |
| Pseudomonas aeruginosa BMH #10 | 100 | p.p.m. |
| Proteus vulgaris Abbott JJ | 3.1 | p.p.m. |
| Proteus mirabilis Fin #9 | 6.2 | p.p.m. |
| Salmonella typhimurium Ed. #9 | 6.2 | p.p.m. |
| Diplococcus pneumoniae 6301 | 25* | p.p.m. |

*tube dilution test; broth container with 20% horse serum

As will be noted by those skilled in the art, the free base of the compound can easily be prepared from the above hydrobromide salt. In turn, the hydrobromide can be converted into other addition salts to produce stable, non-toxic salts that may be used in vivo as antibacterials. Salts, such as the hydrochloride salt, the succinate, tartrate, phosphate, sulfate, citrate and others are particularly well suited as salts for administration of the above compound to warm-blooded animals.

It will be readily understood and appreciated that the above 12a-deoxy-chelocardin may exist in more than one optical form. Also, the change in the C-ring may cause various shifts in resonance forms in the molecule. All of these tautomeric forms and optical isomers are intended to be included in the following claims.

We claim:

1. The compound of the formula

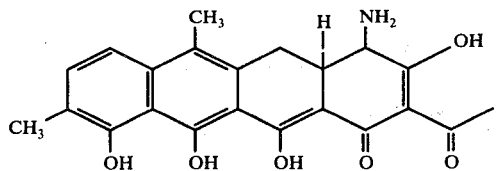

and an acid addition salt thereof.

2. The compound of claim 1 wherein said acid addition salt is prepared from a physiologically acceptable acid.

3. The compound of claim 2 wherein said acid is hydrochloric acid.

* * * * *